United States Patent [19]

Nieh et al.

[11] Patent Number: 5,344,996
[45] Date of Patent: Sep. 6, 1994

[54] CATALYST REMOVAL FROM ALCOHOL ALKOXYLATES USING ACID CLAYS

[75] Inventors: Edward C. Nieh; Michael Cuscurida, both of Austin, Tex.

[73] Assignee: Texaco Chemical Company, White Plains, N.Y.

[21] Appl. No.: 955,214

[22] Filed: Oct. 1, 1992

Related U.S. Application Data

[63] Continuation-in-part of Ser. No. 778,545, Oct. 18, 1991, abandoned.

[51] Int. Cl.$^5$ .................. C07C 43/11; C07C 41/00
[52] U.S. Cl. .................... 568/621; 568/699; 568/608
[58] Field of Search ............ 568/621, 618, 608, 699

[56] References Cited

U.S. PATENT DOCUMENTS

| | | | |
|---|---|---|---|
| 4,507,475 | 3/1985 | Straehle et al. | 568/621 |
| 4,528,364 | 7/1985 | Prier | 568/621 |

FOREIGN PATENT DOCUMENTS 0418533  3/1991  European Pat. Off. .

OTHER PUBLICATIONS

*Kirk-Othmer Encyclopedia of Chemical Technology,* Third Edition, vol. 6, Wiley-Interscience, New York, 1978, W. D. Keller, "Clays" pp. 190–206.
*Chemical Abstracts,* vol. 74, No. 12, Mar. 22, 1971, Columbus, Ohio, Abstract No. 54415k.
*Patent Abstracts of Japan,* vol. 5, No. 71 (C-54)(743), May 13, 1981, JP-A-56-022,323.
O. Neumüller, *Rompps Chemie-Lexicon, Achte Auflage,* Band 2, 1979, Franckh'sche Verlagshandlung Stuttgart, p. 1162, col. 2.

*Primary Examiner*—Johann Richter
*Assistant Examiner*—Rebecca Cook
*Attorney, Agent, or Firm*—Russell R. Stolle; David L. Mossman

[57] ABSTRACT

The removal of basic alkaline earth metal catalysts from alcohol alkoxylate product streams using acid days wetted with water is described. The catalyst level may be reduced to 1 ppm or less in many instances. Effective acid days include, but are not limited to silica days, silica magnesia clays, alumina, montmorillonite days, mixtures thereof and the like. Contacting of the day with the alcohol alkoxylate may take place at ambient to 120° C.

9 Claims, No Drawings

CATALYST REMOVAL FROM ALCOHOL ALKOXYLATES USING ACID CLAYS

This application is a continuation-in-part of application Ser. No. 07/778,545, now abandoned.

Field of the Invention

The invention relates to processes for removing catalysts from product streams, and in one aspect, more particularly relates to removing basic soluble catalysts from alcohol alkoxylate products.

Background of the Invention

An ever-present issue in chemical synthesis is the removal of residual materials from the products. Often such residual materials are unwanted by-products, but they also take the form of catalysts used in the production process. If the catalyst is a solid entrained in a liquid product, its removal is straight-forward. If, however, the catalyst is soluble in the product, then its separation is often more problematic.

Precipitation is sometimes used to remove impurities. For example, U.S. Pat. No. 4,329,515 teaches that basic compounds of Ba and Sr used in the production of peaked alcohol alkoxylates can be removed from the products by precipitating with some polybasic organic acids. Examples of effective acids include glutaric, diglycolic, adipic and azelaic acids. See also U.S. Pat. No. 4,396,779 which describes a process for the preparation of alkanol alkoxylates, useful as nonionic surfactants, which comprises steps for alkoxylating one or more alkanols having a carbon number in the range from 8 to 18 by reaction with one or more alkylene oxides having a carbon number in the range from 2 to 4 under alkaline pH and in the presence of one or more soluble compounds of calcium. The resulting alkoxylation mixture is neutralized by addition thereto of an acid selected from the group consisting of propionic acid, benzoic acid and mixtures thereof. The products are characterized by a single liquid phase of low viscosity.

Of particular concern is the removal of basic catalysts, such as alkaline earth catalysts from alcohol alkoxylate products. These basic catalysts are used to catalyze the addition of an alkylene oxide to the alcohol. Commercial products which have been tested have been found to have 7 to 8 ppm of the alkaline earth metals calcium and strontium. It would be desirable if these catalysts could be removed to a greater extent, and if the product could be neutralized, but without leaving any of the neutralizing agent itself in the product. Levels of alkaline earth catalysts on the order of 7 to 8 ppm will undesirably interfere with subsequent alkoxylation of the products using a different catalyst. It will be understood, however, that in some cases a level of equal to or less than 20 ppm will be acceptable, such as for detergent applications. Typically, above 20 ppm, the alcohol alkoxylate products tend to have a hazy appearance, which is not desirable in detergent applications.

U.S. Pat. No. 4,254,287 teaches the removal of barium catalyst from ethoxylated alcohols prepared using these catalysts by admixing the ethoxylated alcohols with water and mineral acid to precipitate the barium catalyst as a solid then centrifuging to remove the precipitate. However, this process uses an excess of acid and water. The acid excess may remain in the product in undesirable quantities and may produce unwanted by-products. That is, the barium precipitate may be soluble to some extent, which may not be preferred. Additionally, the levels of barium catalyst content may remain in the range of about 10 to 5 ppm using this process, which is still higher than desired for some applications.

Summary of the Invention

Accordingly, it is an object of the present invention to provide a means for quickly and substantially completely removing basic alkaline earth catalysts from alcohol alkoxylate products.

It is another object of the present invention to provide a method for removing basic alkaline earth catalysts from alcohol alkoxylate products using a neutralizing and absorbing agent; but without leaving any of the agent in the alcohol alkoxylate products.

Another object of the invention is to provide a process for removing basic alkaline earth catalysts from alcohol alkoxylate products which does not introduce new by-products into the products.

In carrying out these and other objects of the invention, there is provided, in one form, a process for removing residual basic alkaline earth catalysts from alcohol alkoxylate products containing the same, involving the steps of first wetting an acid clay with water, second contacting an alcohol alkoxylate product containing at least one basic alkaline earth catalyst with the wet acid clay, and third recovering a purged alcohol alkoxylate product where the basic alkaline earth catalyst is absorbed by the acid clay. The process of this invention for removing residual basic alkaline each catalysts from polyoxy alcohol products is conducted in the absence of a soluble acid.

Detailed Description of the Invention

It has been discovered that acid clays, when wet with water, remove basic alkaline earth catalysts from alcohol alkoxylates. Very low levels of the alkaline earth catalyst in the final product, on the order of about 1 ppm or even less, may be achieved with this technique. These low levels are important in the event subsequent alkoxylation using a different catalyst is desired and the catalysts may conflict or interfere with each other. The wet acid clay functions as both a neutralizer and absorbent of basic barium, strontium, calcium and the like. No residual neutralizing agent is left in the product, which is very important in the event that further alkoxylation using a different catalyst is desired. Thus, no undesirable neutralizing agent exists as in some prior art methods which may have residual carboxylic acids. Since the present inventive process is conducted in the absence of a soluble acid, thus undesirable acid neutralizing agents do not remain in the product. This invention is useful in the production of narrow oligomer alkoxylates by a basic alkaline earth catalyzed alkoxylation reaction, but is not necessarily limited thereto. By "narrow" oligomer alkoxylates are meant alkoxylates having from about 3 to about 12 moles of alkylene oxide added thereto. It is expected that in additions of more than 12 moles of alkylene oxide, the catalyst removal technique of this invention would continue to perform well.

While any alkoxylated alcohol product may benefit from the inventive wet acid treatment, ethoxylated alcohols are preferred. The alkylene oxide used to react with the alcohol may be ethylene oxide, propylene oxide or butylene oxide and the like and even mixtures thereof. The alcohols used, whether ethoxylated or reacted with another alkylene oxide, may have molecular weights of up to 200, and may include, but are not limited to, materials such as nonylphenol. In other words, the alcohols may have up to eighteen carbon atoms in their structure.

The effective amount of water used to wet the clay prior to use should be at least enough to saturate and coat the surface of the clay, but an excess of water could also be used. The temperature of the treatment should be from about ambient to 120° C. A more preferred temperature range is from about 80 to about 100° C. The treating process may be carried out in a pressure range where substantial quantity of the Water used in the process remains in the liquid phase. In normal practice, the contact time of the crude product with the clay is about 30 minutes, with a general range of from about 15 to 40 minutes, although it should be understood that these suggested times are not limiting upon the invention. The contact times may be longer or shorter than these. Without being restricted to any particular mechanism, it is believed that many processes happen during contact of the alcohol alkoxylate products with the clay, including, but not limited to hydrolyzing the clay, absorbing alkaline earth metal catalysts into the clay and coagulating or reconstituting the clay.

The acid clays suitable for use in this invention include, but are not necessarily limited to silica clay, magnesia clay, silica magnesia clay, alumina clay, montmorillonite clay, and mixtures thereof. Clays which swell are not preferred in the application of the invention. It is much preferred that clays which have exchangeable proton sites are used, and the above list meets this suggested parameter. Preferably, the acid clay should have a pH in the range of about 7 or less. Clays which interact adversely with the materials of the reaction of interest are to be avoided.

The invention will be illustrated further in the following Examples which are not meant to be limiting, but merely exemplary thereof.

EXAMPLE 1

A mixture of 37.5 grams of calcium ethoxide (prepared from calcium metal and ethanol) and 1980 grams of EPAL 1214 alcohol was charged to a 2 gallon kettle and heated to 120° C. at 20 mm Hg. for 30 minutes. Ethylene oxide was charged to 60 psig pressure while the exothermic reaction brought the temperature to 140° C. Thereafter, the addition of ethylene oxide, a total of 2925 grams was carried out at 140° C. and 60 psig over a period of five hours. To the reaction mixture was added 250 grams of non-wetted Magnesol, a synthetic silica magnesia clay, and then the mixture was stirred at 90° C. under a nitrogen atmosphere for a period of one hour. The product after filtration appeared cloudy.

The product was returned to the kettle and stirred with 250 grams of wet Magnesol (dampened with water prior to use) at 90°-95° C. under nitrogen atmosphere for a period of two hours. Then the mixture was evacuated to 20 mm Hg at 120° C. for 30 minutes and filtered. The calcium content in the product was reduced from 2295 ppm to 1 ppm by such treatment.

EXAMPLE 2

A three mole ethoxylate of EPAL 1214 alcohol was prepared in substantially the same manner as described in Example 1 from 1872 grams of EPAL 1214 alcohol, 2956 grams of ethylene-oxide and 12.8 grams of calcium ethoxide catalyst. The product after being treated with 250 grams of dry Magnesol contained 1060 ppm of calcium. By the procedure described in Example 1, the product after being treated with 250 grams of wet Magnesol contained 1 ppm calcium according to atomic absorption analysis. Atomic absorption was the analytical technique used on all examples.

EXAMPLE 3

A seven mole ethoxylate of EPAL 1214 alcohol was prepared from 1892 grams of EPAL 1214, 2964 grams of ethylene oxide and 7.8 grams of strontium ethoxide in substantially the same manner as described in Example 1, except that the ethoxylation was carried out at 165° C. and 60 psig. After wet Magnesol neutralization, the strontium content in the filtered product was reduced from 1600 to 3 ppm. All of the clay in this and subsequent examples was wetted.

EXAMPLES 4–16

The procedure of Example I was followed to produce a 7.0 mole ethoxylate of EPAL 1214 which was only treated with the wet add clay noted in Table I below. It will be appreciated that the use of the various wet acid clays can reduce the catalyst residue to even less than 1 ppm.

TABLE I

| | Post Reaction Catalyst Removal Studies | | | |
|---|---|---|---|---|
| Ex. | Catalyst Residue | Agent | Residue before, ppm | Residue after, ppm |
| 4 | Cesium | Magnesol | 642 | <1 |
| 5 | Cesium | Magnesol | 803 | <1 |
| 6 | Barium | Alumina | 870 | 120 |
| 7 | Barium | Montmorillonite | 875 | 20 |
| 8 | Barium | Magnesol | 990 | 8 |
| 9 | Strontium | Alumina | 810 | 8 |
| 10 | Strontium | Montmorillonite | 810 | <1 |
| 11 | Calcium | Alumina | 3700 | <1 |
| 12 | Calcium | Montmorillonite | 3700 | 52 |
| 13 | Calcium | Magnesol | 2100 | 1.9 |
| 14 | Magnesium | Alumina | 1760 | <1 |
| 15 | Magnesium | Montmorillonite | 1760 | <1 |
| 16 | Magnesium | Magnesol | 1760 | <1 |

It may be seen that the wet acid clays consistently remove various basic alkali earth materials to very low levels.

Many modifications may be made in the process of this invention without departing from the spirit and scope thereof which are defined only in the appended claims. For example, one skilled in the art may discover that certain reaction conditions or certain acid clays or combinations thereof may give particularly advantageous results.

GLOSSARY

| | |
|---|---|
| EPAL TM 1214 | A 12 to 14 carbon linear primary alcohol mixture with equivalent weight of 197 sold by Ethyl Corp. |
| Magnesol | A synthetic silica magnesia clay available from Reagent Research & Chemical Co. |

I claim:

1. A process for removing residual basic alkaline earth catalysts from alcohol alkoxylate products made from alcohols having up to 18 carbon atoms containing the same, comprising the steps of:

wetting an acid clay with water to saturate and coat the surface of the clay;

contacting an alcohol alkoxylate product made from alcohols having up to 18 carbon atoms containing at least one basic alkaline earth catalyst with the wet acid clay; and recovering a purged alcohol alkoxylate product made from alcohols having up to 18 carbon atoms.

2. The process of claim 1 where the acid clay is selected from the group consisting of silica clay, magnesia clay, silica magnesia clay, alumina clay and montmorillonite clay, or mixtures thereof.

3. The process of claim 1 where the clay has a pH and the pH is 7 or below and where the clay does not swell in the presence of alcohol alkoxylates.

4. The process of claim 1 where the process is conducted at a temperature in the range from about ambient to 120° C.

5. Te process of claim 1 where the amount of basic alkaline earth catalyst within the purged polyalkoxylate product is equal to or less than about 1 ppm.

6. A process for removing residual basic alkaline earth catalysts from alcohol alkoxylate products made from alcohols having up to 18 carbon atoms containing the same, comprising the steps of:

wetting an acid clay with water to saturate and coat the surface of the clay, where the acid clay has a pH of 7 or less and is selected from the group consisting of silica clay, magnesia clay, silica magnesia clay, alumina clay, montmorillonite clay, and mixtures thereof;

contacting an alcohol alkoxylate product made from alcohols having up to 18 carbon atoms containing at least one basic alkaline earth catalyst with the wet acid clay; and recovering a purged alcohol alkoxylate made from alcohols having up to 18 carbon atoms.

7. The process of claim 6 where the process is conducted at a temperature in the range from about 80 to 120° C.

8. The process of claim 6 where the amount of basic alkaline earth catalyst within the purged polyalkoxy products is equal to or less than about 1 ppm.

9. A process for removing residual basic alkaline earth catalysts from alcohol alkoxylate products made from alcohols having up to 18 carbon atoms containing the same, comprising the steps of:

wetting an acid clay with water to saturate and coat the surface of the clay, where the acid clay has a pH of 7 or less and does not swell in the presence of alcohol alkoxylates, and is selected from the group consisting of silica clay, magnesia clay, silica magnesia clay, alumina clay, montmorillonite clay, and mixtures thereof;

contacting an alcohol alkoxylate product made from alcohols having up to 18 carbon atoms containing at least one basic alkaline earth catalyst with the wet acid clay at a temperature in the range from about 80 to 120° C.; and recovering a purged alcohol alkoxylate product where the basic alkaline earth catalyst is absorbed by the wet acid clay and the amount of basic alkaline earth catalyst within the purged alcohol alkoxylate product made from alcohols having up to 18 carbon atoms.

* * * * *

UNITED STATES PATENT AND TRADEMARK OFFICE
CERTIFICATE OF CORRECTION

PATENT NO.   : 5,344,996
DATED        : September 6, 1994
INVENTOR(S)  : Edward C. Nieh, et al.

It is certified that error appears in the above-identified patent and that said Letters Patent is hereby corrected as shown below:

At the Abstract, line 2, please delete "days" and insert --clays-- therefor.

At the Abstract, line 5, at both occurrences, please delete "days" and insert --clays-- therefor.

At the Abstract, line 6, please delete "days" and insert --clays-- therefor.

At the Abstract, line 7, please delete "day" and insert --clay-- therefor.

At column 2, line 30, please delete "day" and insert --clay-- therefor.

At column 2, line 36, please delete "days" and insert --clays-- therefor.

At column 2, line 44, please delete "day" and insert --clay-- therefor.

At column 3, line 6 please delete "day" and insert --clay-- therefor.

At column 3, line 15, please delete "day" and insert --clay-- therefor.

At column 3, line 22, please delete "day" and insert --clay-- therefor.

At column 3, line 23, please delete "day" and insert --clay-- therefor.

At column 3, line 12, delete the period, after --The--.

UNITED STATES PATENT AND TRADEMARK OFFICE
CERTIFICATE OF CORRECTION

PATENT NO.   : 5,344,996
DATED        : September 6, 1994
INVENTOR(S)  : Edward C. Nieh, et al.

It is certified that error appears in the above-identified patent and that said Letters Patent is hereby corrected as shown below:

At column 3, line 24, please delete "day" and insert --clay-- therefor.

At column 3, line 25, please delete "day" and insert --clay-- therefor.

At column 3, line 26, please delete "days" and insert --clays-- therefor.

At column 3, line 28, please delete "day" and insert --clay-- therefor.

At column 3, line 29, please delete "day" and insert --clay-- therefor.

At column 3, line 31 please delete "days" and insert --clays-- therefor.

At column 4, line 17, please delete "day" and insert --clay-- therefor.

At column 4, line 26 please delete "days" and insert --clays-- therefor.

Signed and Sealed this

Thirteenth Day of June, 1995

Attest:

BRUCE LEHMAN

*Attesting Officer*   Commissioner of Patents and Trademarks